United States Patent [19]

Nakamura et al.

[11] Patent Number: 5,817,839
[45] Date of Patent: Oct. 6, 1998

[54] DOUBLE-CHAIN TYPE SULFATED COMPOUNDS HAVING ACID DEGRADABILITY AND PROCESS FOR PRODUCING THE SAME

[75] Inventors: Masaki Nakamura, Takatsuki; Daisuke Ono, Toyonaka; Jia-he Qian, Yamatotakada; Hiromitsu Seike, Nara-ken; Shigeo Mizutani, Katano; Takeshi Munekiyo, Yao, all of Japan

[73] Assignees: Matsumoto Yushi-Seiyaku Co., Ltd.; Osaka Municipal Government, both of Osaka, Japan

[21] Appl. No.: 980,203

[22] Filed: Nov. 28, 1997

Related U.S. Application Data

[63] Continuation-in-part of Ser. No. 780,467, Jan. 8, 1997, abandoned.

[30] Foreign Application Priority Data

Jan. 11, 1996 [JP] Japan ..................................... 8-002938

[51] Int. Cl.⁶ .................................................. C07D 319/04
[52] U.S. Cl. ............................................................ 549/374
[58] Field of Search ............................................. 549/374

[56] References Cited

U.S. PATENT DOCUMENTS 3,169,879  2/1965  Wahl et al. ............................... 106/176

OTHER PUBLICATIONS

Chemistry Express, vol. 7, No. 8, pp. 637–640 (1992) Kinki Chemical Society, Japan.

J. Am. Oil Chem. vol. 69, No. 1, pp. 30–33 (Jan. 1992).

J. Am. Oil Chem. vol. 69, No. 7, pp. 626–632 (Jul. 1992).

J. Jpn. Oil Chem. vol. 40, pp. 473–477 (1991).

*Primary Examiner*—Deborah C. Lambkin
*Assistant Examiner*—Laura L. Stockton
*Attorney, Agent, or Firm*—Stevens, Davis, Miller & Mosher, L.L.P.

[57] ABSTRACT

Described herein are sulfated compounds represented by the formula (I):

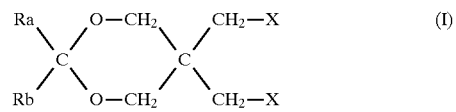

wherein X respectively represent —OSO$_3$M or a hydroxyl group and at least one of X represents —OSO$_3$M, a process for producing the sulfated compounds and a process for decomposing the sulfated compounds in an aqueous acid solution.

5 Claims, No Drawings

DOUBLE-CHAIN TYPE SULFATED COMPOUNDS HAVING ACID DEGRADABILITY AND PROCESS FOR PRODUCING THE SAME

This application is a CIP of 08/780,467 filed Jan. 8, 1997, now abandoned.

BACKGROUND OF THE INVENTION

1. Field of the Invention

The present invention relates to a double-chain type sulfate surfactant having a 1,3-dioxane ring in the molecule, which is useful as a novel surfactant.

2. Prior Art

Heretofore, surfactants have been used in various fields such as industrial applications (e.g. washing, emulsification, dispersion, flotation, etc.), household applications and the like. However, it is very difficult to perform disposal of waste water after using for washing and flotation etc. because the surf actant is water-soluble and, therefore, the improvement has been required. When using a polymer coagulant or when waste water contains an anionic surf actant, disposal of waste water is performed by introducing a large amount of calcium salts or magnesium salts to insolubilize the surfactant, at present. However, these processes are not only very expensive, but non-efficient in view of a disposal effect.

SUMMARY OF THE INVENTION

An object of the present invention is to provide a surfactant whose disposal (e.g. recovery) can be easily performed even if it is contained in waste water, and a process for decomposing the surfactant.

The present invention relates to sulfated compounds represented by the formula (I):

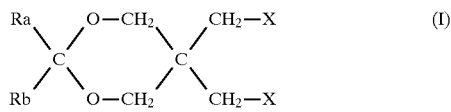

wherein Ra and Rb may be the same or different and respectively represent a $R^1(OR^2)_z$ group which bonds to a carbon atom at the 2-position constituting a 1,3-dioxane ring;

$R^1$ represents a linear chain or branched alkyl or alkenyl group having 1 to 22 carbon atoms, and may contain an aromatics in a structural formula;

$R^2$ represents an alkylene group having 2 to 4 carbon atoms;

z represents an integer of 0 to 20 as an average value; and

M represents a hydrogen atom, an alkaline metal, ammonium, a mono-, di- or trialkanol ammonium having 2 to 3 carbon atoms, an alkyl-substituted ammonium having 1 to 5 carbon atoms or a basic amino acid group.

The present invention also relate to a process for producing the sulfated compounds the formula (I), which comprises sulfating a diol having a 1,3-dioxane ring represented by the formula (II):

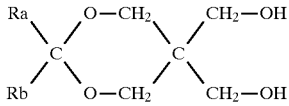

with a sulfating agent.

The present invention also relates to a process for decomposing the compound (I), which comprises adding an acid in an aqueous solution containing the compound (I) to acidify the aqueous solution, thereby decomposing the compound (I) into a ketone and a sulfated diol.

The novel compound (I) having a surfactant activity of the present invention has a ketal skeleton (1,3-dioxane ring in the present compound) in the molecule, which is easily decomposed by an action of an acid and has a structure capable of being decomposed easily and rapidly into a ketone and a diol only by treating with an acid after accomplishing the intended object. As is apparent from the following Examples, the compound is easily decomposed under an acid condition. Long-chain ketone compounds among decomposition products are water-insoluble and can be easily removed from waste water. The diol derivatives remain in waste water but the loading drastically decreases in comparison with an initial concentration of the surfactant and, therefore, the disposal of the diol becomes easier.

Furthermore, the compound (I) having an anionic surfactant activity of the present invention has the following specific structure which is different from that of a normal surfactant. That is, the compound has two hydrophobic chains and two hydrophilic groups in one molecule and has a specific structure wherein two normal surfactants are bonded.

DETAILED DESCRIPTION OF THE INVENTION

The compound of the present invention is a surfactant which is superior in low-temperature solubility and has good surfactant activity at low concentration and good surface tension reduction activity in common with the compound disclosed in literatures such as Chemistry Express, 7, 637 (1992), J. Am. Oil Chem. Soc. 69, 30 (1992), J. Am. Oil Chem. Soc. 69, 626 (1992), J. Jpn. Oil Chem. Soc., 40, 473 (1991) and the like.

In the compound (I) of the present invention, examples of preferred Ra and Rb include pentyl, hexyl, nonyl, undecyl, tridecyl, pentadecyl, heptadecyl, nonadecyl, 8-heptadecenyl and the like. Particularly preferred examples include undecyl, tridecyl, pentadecyl and 8-heptadecenyl. Further, sulfates (I) in which Ra is a methyl group and Rb represents a $R^1(OR^2)_z$ group which bonds to a carbon atom at 2-position constituting a 1,3-dioxane ring; R1 represents a linear chain or branched alkyl or alkenyl group having 6 to 22 carbon atoms, and may contain an aryl group in a structural formula; R2 represents an alkylene group having 2 to 4 carbon atoms; z represents an integer of 0 to 20 as an average value are easily decomposed by acids, and have an extremely high solubility in cold water. The ability of decreasing surface tension thereof is lower than that of sulfates such as X or XI show surface activity at a lower concentration by one order than conventional anionic surface active agents do, and the ability of decreasing surface tension thereof is similar to a conventional one. Examples of the preferred group for M include sodium, potassium, lithium, ammonium, diethanol ammonium and triethanol ammonium. Among them, sodium, potassium and diethanol ammonium are particularly preferred.

The compound (I) of the present invention is produced by sulfating a diol (II) having a 1,3-dioxane ring, which is a compound formed by subjecting a long-chain ketone compound of the formula (III) and pentaerythritol to a dehydration reaction in the presence of an acid catalyst, with a sulfating agent.

The acid catalyst used herein is an acid catalyst which is normally used, such as sulfuric acid, hydrochloric acid, p-toluenesulfonic acid, boron trifluoride and the like. The dehydration reaction may be performed in the absence of a solvent, but a dehydration reaction performed under an azeotropic condition using a solvent (e.g. DMF, xylene, toluene, benzene, dimethylacetamide, etc.) is preferred.

In the above production process, the sulfating reaction of the compound (II) is preferably performed by reacting the compound (II) with a sulfating agent of at least one compound selected from the group consisting of addition products of $YSO_3H$ (provided that Y represents a halogen atom), $SO_3$ and $H_2NSO_3$ with a Lewis base.

The compound of the present invention is a compound of the formula (I) wherein one or two of X are —$OSO_3M$. A compound wherein both of X are —$OSO_3M$ is most preferred, but one of X may be —$OSO_3M$. In latter case, a compound wherein the other of X is a hydroxyl group is preferred.

As shown in the following reaction scheme (IV):

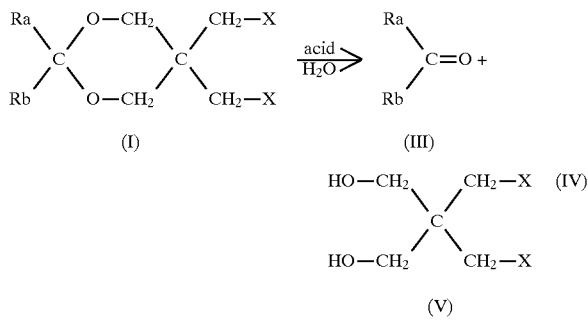

the compound (I) of the present invention is an acid decomposition type compound which is characterized by being decomposed into an ketone (III) and a sulfated diol (V) as a starting substance in an aqueous acid solution. Regarding the compound (V), the case where both sulfuric groups are decomposed according to the condition of the acid decomposition and both of X are hydroxyl groups is included.

As the acid used for decomposing the compound (I) under the acid condition, organic acids (e.g. oxalic acid, citric acid, acetic acid, etc.) can also be used, in addition to acid substances which are normally used (e.g. hydrochloric acid, sulfuric acid, nitric acid, phosphoric acid, toluenesulfonic acid, polyphosphoric acid etc.). Particularly preferred acids are hydrochloric acid, sulfuric acid and phosphoric acid.

An acidity (pH) for accelerating the decomposition is not more than 5.5, preferably not more than 4.0.

The following Examples further illustrate the present invention in detail.

EXAMPLE 1

The following illustrates synthesis route of the double-chain type sulfated compounds of the present invention.

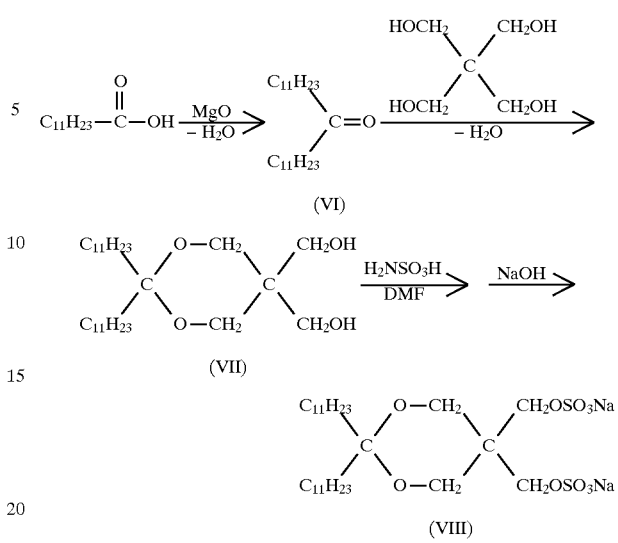

Synthesis of 12-tricosanone (VI)

Lauric acid (50 g, 0.25 mol) and magnesium oxide (12.6 g, 0.3125 mol) were charged in a 500 ml round bottom flask equipped with an air condenser having a length of 50 cm, and then the mixture was heated at 300° to 320° C. for 8 hours using a heating mantle. After the completion of the reaction, the reaction solution was cooled. Then, 250–300 ml of n-hexane was added and the reaction solution was sufficiently dissolved in n-hexane with heating. The resulting solution was filtered in a hot state and about 200 ml of an aqueous 4N-sulfuric acid solution was added to the filtrate, followed by sufficiently stirring to decompose unreacted magnesium laurate. The hexane layer was separated, washed with water, and then washed with 200 ml of an aqueous 5% NaOH solution to remove dissolved lauric acid. The hexane layer was washed again with water, dried over anhydrous sodium sulfate and filtered, and then hexane was removed by using a rotary evaporator to isolate a reaction product. The resulting product was recrystallized from a mixed solvent of ethanol and benzene in the ratio of 2:1 to obtain 32.9 g of 12-tricosanone as a white flakelike crystal (yield 77.8%).

The characteristic values of the formed 12-tricosanone are as follows:

Infrared absorption spectrometry (KBr disk method) 1705 $cm^{-1}$ (ketone absorption)

Proton nuclear magnetic resonance spectrometry ($CDCl_3$ solution):
0.88 ppm (t, J=6.6Hz, 6H)
1.26 ppm (s, 32H)
1.56 ppm (m, 4H) (β-methylene of carbonyl)
2.37 ppm (t, J=7.4Hz, 4H) (α-methylene of carbonyl)
Melting point: 68.4° C.

Synthesis of 2,2-diundecyl-5,5-bis(hydroxymethyl)-1,3-dioxane (VII)

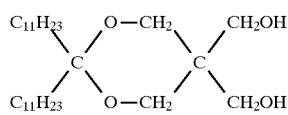

(VII)

12-Tricosanone (2.5 g, 7.4 mmol), pentaerythritol (1.5 g, 11.0 mmol), p-toluenesulfonic acid monohydrate (150 mg; 0.79 mmol) and a mixture of dimethylacetamide (20 ml) and xylene (10 ml) were charged in a 200 ml flask equipped with an azetropic distillation apparatus, and then the mixture was reacted with heating at a bath temperature of 178° to 180° C. in a nitrogen atmosphere for about 25 hours. Since a theoretical amount of water is separated, the reaction was terminated at this point and the reaction solution was cooled. Then, 3 ml of an 1N-NaOH solution was added to alkalify the reaction solution. After the solvent was removed from the reaction solution using a rotary evaporator, the reaction residue was repeatedly extracted with n-hexane to recover the product. The hexane solution was analyzed by gas chromatography. As a result, it was confirmed that desired 2,2-diundecyl-5,5-bis(hydroxymethyl)-1,3-dioxane (VII) is obtained in the yield of 93.8%. Although about 6% of the unreacted ketone is present, it can be easily separated and purified into a ketone and diol as the product by silica gel chromatography, if necessary.

The characteristic values of 2,2-diundecyl-5,5-bis(hydroxymethyl)-1,3-dioxane (VII) purified by silica gel chromatography are as follows:

Infrared absorption spectrometry (NaCl thin-layer method):
3294 cm$^{-1}$ (—OH absorption)
1145 cm$^{-1}$ (ether absorption)
1095 cm$^{-1}$ (ether absorption)
1045 cm$^{-1}$ (ether absorption)

Proton nuclear magnetic resonance spectrometry (CDCl$_3$ solution):
0.88 ppm (t, J=6.6Hz, 6H)
1.26 ppm (s, 36H)
1.67 ppm (m, 4H)
3.70 ppm (s, 4H) (2×—O—C$\underline{H}_2$—C)
3.74 ppm (s, 4H) (2×—C$\underline{H}_2$—OH)

Synthesis of sulfated substance (VIII)

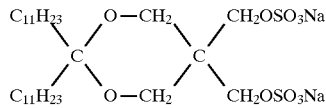

(VIII)

2,2-Diundecyl-5,5-bis(hydroxymethyl)-1,3-dioxane (VII) (2 g, 4.38 mmol) was charged in a 50 ml round bottom flask and 10 ml of anhydrous DMF and 1 ml of absolute pyridine were added, followed by dissolving 2,2-diundecyl-5,5-bis(hydroxymethyl)-1,3-dioxane. To this solution was added sulfamic acid (935 mg, 9.63 mmol), followed by heating from room temperature to 60° C. with cutting off moisture in air over one hour. After the reaction was continued at 60° C. for about 4 hours, an aqueous solution prepared by dissolving 500 mg of NaOH in 1 ml of water was added to alkalify the reaction solution. When the reaction solution was cooled to room temperature by standing, crystal was deposited. Therefore, the crystal was filtered and collected to obtain a double hydrophobic chain disodium disulfated salt (VIII) having a 1,3-dioxane ring quantitatively. Since this salt is slightly yellowish, it was recrystallized from hydrous ethanol to obtain a purified white compound. The yield after recrystallization was from 90 to 93%.

The characteristic values of the compound (VIII) are as follows:

Infrared absorption spectrometry (KBR disk method)
1257 cm$^{-1}$ (sulfate absorption)
1244 cm$^{-1}$ (sulfate absorption)
1228 cm$^{-1}$ (sulfate absorption)
1217 cm$^{-1}$ (sulfate absorption)
1078 cm$^{-1}$ (ether absorption)
1072 cm$^{-1}$ (ether absorption)

Proton nuclear magnetic resonance spectrometry (D$_2$O solution, measured at 80° C.):
0.86 ppm (t, J=6.5Hz, 6H)
1.29 ppm (s, 36H)
1.71 ppm (m, 4H)
3.75 ppm (s, 4H) (2×—O—C$\underline{H}_2$—C)
4.04 ppm (s, 4H) (2×—C$\underline{H}_2$—OSO$_3$)

Melting point: 84.7° C.

EXAMPLE 2

The measuring results of the characteristic values of an aqueous solution of the resulting sulfate type compound (VIII) are as follows:

Critical micelle concentration: 1.3×10$^{-5}$ mol/L

Surface tension at critical micelle concentration: 34.9 mN/m

Kraft point (1 wt % concentration): ≦0° C.

EXAMPLE 3

The acid decomposition properties of the resulting compound (VIII) were evaluated in the following manner.

To disodium disulfate (VIII) (0.1 mmol, 66.1 mg) were added 12 ml of an aqueous hydrochloric acid solution and 12 ml of ethyl ether, and then the mixture was stirred at room temperature (25° C.) for a predetermined time. The formed 12-tricosanone was quantitatively determined by gas chromatography using n-tetracosane as an internal standard substance to measure a percentage of decomposition. The measuring results are shown below.

| Concentration of aqueous hydrochroric acid solution | Decomposition time | Percentage decomposition (%) |
|---|---|---|
| 0.5N | 1 hour | 90.3 |
| 1.0N | 1 hour | 93.7 |

EXAMPLE 4

Three kinds of ketones (Ra is methyl and Rb is C9, C11 or C13 alkyl) are used to obtain six acid decomposable sulfated compounds by following methods.

synthesis of 2-methyl-2-alkyl-5,5-bis(hydroxymethyl)-1,3-dioxane (IX):

The titled compounds were prepared according to the same manner as Example 1 except that the aforementioned ketones were used instead of 12-tricosanone (VI), and DMF and toluene as solvents. The products contained bisdioxane of about 7 to 9% by weight, which could be easily purified by recrystallization from ethanol/hexane. The yields of titled compounds were 92.7% for C9, 90.0% for C11 and 99.5% for C13 respectively.

synthesis of disulfated compound (X):

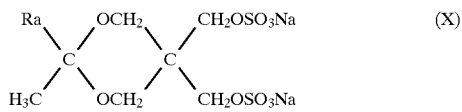

The titled compound was prepared according to the same manner as Example 1 except that the 2-methyl-2-alkyl-5,5-bis(hydroxymethyl)-1,3-dioxane (IX) was used instead of 2,2-diundecyl-5,5-bis(hydroxymethyl)-1,3-dioxane (VII). The obtained compound was easily purified by the recrystallization from ethanol/hexane.

Synthesis of monosulfated compound (XI):

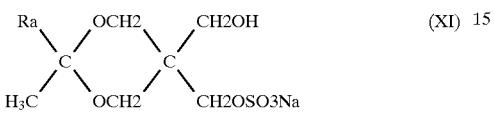

The compound (XI) was prepared according to the preparation of (X) except that the sulfamic acid and NaOH were used by half respectively. The yield of the compound (XI) was 70 to 80%.

Properties of compounds (X) and (XI):

Acid Decomposability:

Compounds (X) and (XI) were dissolved in water respectively, to which hydrochloric acid was added to be controlled to various concentrations and kept with stirring for one hour at room temperature. The both compounds were decomposed at 0.1N HCl, but the compound (XI) (monosulfated compound) was more easily decomposed than disulfated compound (X). The percentage of decomposed compounds were shown below.

| sulfated compounds (X) & (XI) | acid decomposability (conc. (N) of HCl aq. sol.; for one hour) | | |
|---|---|---|---|
| | 1N | 0.5N | 0.1N |
| C9C1-dioxane-monosulfate | 100 | 100 | 100 |
| C11C1-dioxane-monosulfate | 100 | 100 | 100 |
| C13C1-dioxane-monosulfate | 100 | 100 | 100 |
| C9C1-dioxane-disulfate | 97 | 96 | 91 |
| C11C1-dioxane-disulfate | 86 | 84 | 83 |
| C13C1-dioxane-disulfate | 89 | 89 | 90 |

In the above table the expressions C9, C1, C11 and C13 represent nonyl, methyl, undecyl and tridecyl respectively.

Solubility At Low Temperature:

The Kraft points of the above six sulfated compounds (anionic surface active agents) of the present invention were determined at concentration of 1% by weight in water respectively, which were indices of solubility to water thereof. The Kraft points of these six compounds were lower than 0° C. In comparison the kraft point of sodium dodecyl sulfate which is one of typical anionic surface active agents was 16° C.

In general an anionic surface active agent is inferior in the solubility at low temperature, which has been said as one of defects of an anionic surface active agent. In spite of such a common view it has become apparent that the anionic surface active agents of the present invention exhibit excellent solubility to water even at low temperature such as ice water. Therefore, using the sulfated compounds of the present invention any formulations can be stably prepared without fear of gelation and deposition of insoluble materials, which is industrially beneficial.

Ability Of Decrease Of Surface Tensions

The critical micelle concentration (CMC) of each above sulfated compound and the surface tension at the CMC ($\gamma$cmc) were determined at 25° C. according to Wilhelmy method. The results were shown below.

| sulfated compounds | | |
|---|---|---|
| | CMC (mol/l) | $\gamma$cmc (mN/m) |
| C9C1-dioxane-monosulfate | $5.4 \times 10^{-3}$ | 37.1 |
| C11C1-dioxane-monosulfate | $7.0 \times 10^{-4}$ | 38.6 |
| C13C1-dioxane-monosulfate | $1.6 \times 10^{-4}$ | 41.0 |
| C9C1-dioxane-disulfate | $9.8 \times 10^{-3}$ | 42.0 |
| C11C1-dioxane-disulfate | $5.8 \times 10^{-3}$ | 43.0 |
| C13C1-dioxane-disulfate | $3.6 \times 10^{-3}$ | 44.7 |
| sodium dodecyl sulfate | $8.2 \times 10^{-3}$ | 38.5 |

As apparent from the above results monosulfates represented lower CMC, which means they have activity even at lower concentration, and lower surface tension, whereas disulfates represented higher CMC and higher surface tension than the monosulfates.

Foaming Ability

The foaming ability of the above six sulfated compounds was determined according to an air bubbling method, in which 5 ml of 0.1 wt. % aqueous solution of the sulfated compounds were put in a small cell respectively and kept at 25° C., and 250 ml of air was blown into the cell over one minute through a glass capillary which was installed through the bottom of the cell to generate foam. The volume of the foam was measured by a cylinder at 5 min. and 10 min. after the air-blowing was quitted. The results were shown below.

| sulfated compounds | conc. | volume of foam | | |
|---|---|---|---|---|
| | (wt. %) | 0 min. | 5 min. | 10 min. |
| C9C1-dioxane-monosulfate | 0.5 | 255 | 60 | 40 |
| C11C1-dioxane-monosulfate | 0.1 | 255 | 250 | 240 |
| C13C1-dioxane-monosulfate | 0.1 | 255 | 252 | 240 |
| C9C1-dioxane-disulfate | 1.5 | 20 | 0 | 0 |
| C11C1-dioxane-disulfate | 0.5 | 70 | 0 | 0 |
| C13C1-dioxane-disulfate | 0.5 | 200 | 0 | 0 |
| sodium dodecyl sulfate | 0.1 | 160 | 55 | 30 |
| sodium dodecyl sulfate | 0.5 | 255 | 240 | 230 |
| sodium dodecyl sulfate | 1.5 | 245 | 235 | 220 |

Monosulfates of the present invention have an excellent foaming ability and a foam stability similar to or higher than the sodium dodecyl sulfate which is known as one of anionic surface active agents having an excellent foaming ability.

Stability In Hard Water

Hard water (10000 ppm of $CaCO_3$) was added dropwise to each aqueous solution of the above sulfated compounds (10 mM), and the concentration of $CaCO_3$ at which the solution of the sulfated compound was clouded was determined. Every aqueous solution of the above six compounds was not clouded at 5000 ppm of $CaCO_3$, but an aqueous solution of sodium dodecyl sulfate (10 mM), a typical anionic surface active agent, was clouded at 150 ppm of $CaCO_3$. As apparent from the above results, the sulfated compounds of the present invention have extremely high stability in hard water.

Permeability 0.1–1.5% By weight of aqueous solution of the above sulfated compounds were prepared respectively. 80 Ml of each solution was taken into 100 ml cylinder. A sinker was hung with a thread of 5 cm at one short side of felt (2 cm×5 cm, thickness of 2 mm), so that the felt can be floated on the surface of the aqueous solution remaining 2 mm of top of the felt over the surface. The felt with the sinker was inserted into the cylinder and measured the time till the top of the felt was sunk into the solution completely.

The results were shown below.

| sulfated compounds | | | | |
|---|---|---|---|---|
| | wetting time for felt cloth concentration of surfactants (wt. %) | | | |
| | 0.1 | 0.2 | 0.5 | 1.5 |
| C9C1-dioxane-monosulfate | (2'41") | (41") | 6–7" | — |
| C11C1-dioxane-monosulfate | 16" | 12" | — | — |
| C13C1-dioxane-monosulfate | 16" | 13" | — | — |
| C9C1-dioxane-disulfate | (18'48") | (12'04") | — | 2'32" |
| C11C1-dioxane-disulfate | — | — | 2'00" | — |
| C13C1-dioxane-disulfate | — | — | 1'34" | — |
| sodium dodecyl sulfate | (31") | (12") | 3"–4" | — |

The data in ( ) is one obtained at a concentration of less than cmc. Comparing the permeability at a concentration of not less than cmc monosulfates show the permeability similar to that of sodium dodecyl sulfate but disulfates show lower permeability. Among monosulfates one having the shorter hydrocarbon chain shows the higher permeability.
In the Table the mark "—" means "not determined".

The meaning of the term "aromatic" as used in the present specification and claims is a major group of unsaturated cyclic hydrocarbons containing one or more rings; these are typified by benzene, which has a six-carbon ring containing three double bonds. The vast number of compounds of this important group, derived chiefly from petroleum and coal tar, are rather highly reactive and chemically versatile. The name is due to the strong and not unpleasant odor characteristic of most substances of this nature. Certain 5-membered cyclic compounds such as the furan group (heterocyclic) are analogous to aromatic compounds.

The meaning of the term "basic amino acids" (or "residual group of basic amino acids") as used in the present specification and claims is amino acids in which the number of the amine group is more than the number of the acid group in the amino acids, and it is common term.

What is claimed is:

1. A sulfated compounds represented by the formula (I):

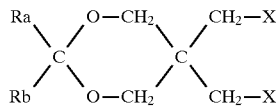

wherein X respectively represents —OSO$_3$M or a hydroxyl group and at least one of X represents —OSO$_3$M;

Ra and Rb may be the same or different and respectively represent a R$^1$(OR$^2$)$_z$ group which bonds to a carbon atom at the 2-position constituting a 1,3-dioxane ring;

R$^1$ represents a linear chain or branched alkyl or alkenyl group having 1 to 22 carbon atoms, and may contain an aromatics in a structural formula;

R$^2$ represents an alkylene group having 2 to 4 carbon atoms;

z represents an integer of 0 to 20 as an average value; and

M represents a hydrogen atom, an alkaline metal, ammonium, a mono-, di- or trialkanol ammonium having 2 to 3 carbon atoms, an alkyl-substituted ammonium having 1 to 5 carbon atoms or a basic amino acid group.

2. A process for producing the sulfated compounds of claim 1, which comprises sulfating a diol having a 1,3-dioxane ring represented by the formula (II):

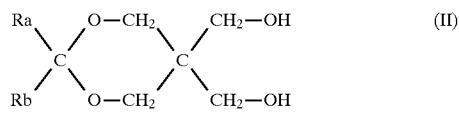

with a sulfating agent.

3. The process for producing the sulfated compounds of claim 2, wherein the compound of the formula (II) is a compound obtained by reacting a long-chain ketone compound represented by the formula (III):

with pentaerythritol in the presence of an acid catalyst.

4. A process for decomposing the compound (I) of claim 1, which comprises adding an acid in an aqueous solution containing the compound (I) to acidify the aqueous solution, thereby decomposing the compound (I) into a ketone and a sulfated diol.

5. Sulfated compounds of claim 1, in which Ra is a methyl group and Rb represent a R$^1$(OR$^2$)$_z$ group which bonds to a carbon atom at 2-position constituting a 1,3-dioxane ring; R$^1$ represents a linear chain or branched alkyl or alkenyl group having 6 to 22 carbon atoms, and may contain an aryl group in a structural formula; R$^2$ represents an alkylene group having 2 to 4 carbon atoms; z represents an integer of 0 to 20 as an average value.

* * * * *